United States Patent
Smith

(10) Patent No.: US 7,479,608 B2
(45) Date of Patent: Jan. 20, 2009

(54) FORCE SWITCH

(75) Inventor: Kevin W. Smith, Coral Gables, FL (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 11/750,622

(22) Filed: May 18, 2007

(65) Prior Publication Data

US 2007/0267281 A1  Nov. 22, 2007

Related U.S. Application Data

(60) Provisional application No. 60/902,534, filed on Feb. 21, 2007, provisional application No. 60/858,112, filed on Nov. 9, 2006, provisional application No. 60/810,272, filed on Jun. 2, 2006, provisional application No. 60/801,989, filed on May 19, 2006.

(51) Int. Cl.
H01H 35/14 (2006.01)
(52) U.S. Cl. .................. 200/61.53; 200/275; 200/16 B
(58) Field of Classification Search ............. 200/61.53, 200/275, 16 B, 532, 67.76, 340
See application file for complete search history.

(56) References Cited

U.S. PATENT DOCUMENTS

| 2,770,964 | A | | 11/1956 | Mercier |
| 4,564,730 | A | * | 1/1986 | Tomizu et al. ............ 200/16 B |
| 4,703,140 | A | * | 10/1987 | Poling ....................... 200/83 P |
| 4,795,863 | A | | 1/1989 | Tomizu et al. |
| 5,505,593 | A | * | 4/1996 | Hartley et al. ............... 417/393 |
| 6,518,528 | B2 | * | 2/2003 | Nickerson et al. ........... 200/447 |
| 2005/0252756 | A1 | | 11/2005 | Kent et al. |

FOREIGN PATENT DOCUMENTS

EP  1728475 A2  12/2006

* cited by examiner

*Primary Examiner*—Kyung Lee
(74) *Attorney, Agent, or Firm*—Mayback & Hoffman, P.A.; Gregory L. Mayback; Scott D. Smiley

(57) ABSTRACT

A mechanical force switch to be disposed along a longitudinal device axis of a medical device includes an electrically conductive switching piston to form a first electrical contact of the switch, a hollow body, an end stop, a bias device, and an electrically conductive second contact of the switch electrically insulated from the piston. The piston is movably disposed in the body hollow along the axis to define different switch-making and -breaking positions. The piston is also movably disposed in a cavity of the stop and the stop is disposed in the body. The stop can be a smooth or threaded puck. The bias device surrounds the piston and imparts bias against it to retain it in one of the two positions until an external axis force overcomes the bias, at which time the switch indicates a state changeover. The switch can be normally open or closed.

22 Claims, 9 Drawing Sheets

FORCE SWITCH

CROSS-REFERENCE TO RELATED APPLICATION

This application claims the priority, under 35 U.S.C. § 119, of U.S. Provisional Patent Application Ser. Nos. 60/801,989 filed May 19, 2006, 60/810,272, filed Jun. 2, 2006, 60/858, 112, filed Nov. 9, 2006, and 60/902,534, filed Feb. 21, 2007, and is related to U.S. patent application Ser. Nos. 11/705,381, 11/705,334, and 11/705,246, all filed Feb. 12, 2007, the entire disclosures of which are all hereby incorporated herein by reference in their entireties.

STATEMENT REGARDING FEDERALLY SPONSORED RESEARCH OR DEVELOPMENT n/a

FIELD OF THE INVENTION

The present invention lies in the field of switches, in particular, a force switch. The device can be used along with any tool in which a particular longitudinal force needs to be overcome prior to reaching a given detected force.

BACKGROUND OF THE INVENTION

In various applications, a compressible material is compressed between two surfaces for modification of the material in some way after being compressed. The material can be compressed too little, too much, or in an acceptable range of compression. It would be beneficial to provide an electrical switch that can indicate when the acceptable minimum compression force has been exceeded. It would further benefit if the switch actuates over a small gap and is longitudinally in-line with the device in which the switch is incorporated. It would also be beneficial if the minimum force setting of the switch could be pre-set to given force values.

BRIEF SUMMARY OF THE INVENTION

The invention overcomes the above-noted and other deficiencies of the prior art by providing an electronic switch that actuates over a small gap (on the order of 25 to 200 micrometers), is longitudinally in-line with the device in which the switch is incorporated, and switches dependent upon a longitudinally expanding external force that can be pre-set over a given floor force value.

A characteristic of the force switch described herein is that the longitudinal forces that the force switch can withstand are significantly higher than that existed in the past. With a force switch having approximately a 6 mm diameter, for example, an approximately 5 to 8 pound longitudinally pulling force changes the switch state while, at the same time, being able to withstand almost 300 pounds of longitudinal pulling or compressive force. This is an almost twenty-fold difference.

There are many uses for the force switch in various different technology areas.

In a first exemplary area of technology, the force switch can be used to measure compressive forces imparted upon tissue by medical devices. In many medical procedures, tissue is compressed between two surfaces before a medical device is caused to make a change in the compressed tissue. If the tissue is compressed too little, then the change sought to be effected might not be sufficient. If the tissue is, on the other hand, compressed too much, the change sought to be effected might actually destroy the area of interest. When compressing such tissue, there are measurable force ranges that fall between these two extremes. Knowing the "safe" force range can allow the user to select a pre-tensioning of the force switch to change its state (i.e., indicate to the user the pre-tensioned force has been exceeded) within the "safe" range of that tissue.

The force switch described herein can be constructed in a customized way to have the state-changing pre-tension match the "safe" range of the tissue to be operated upon.

One type of medical device that is used to change a state of tissue is a medical stapling device. Ethicon Endo-Surgery, Inc. (a Johnson & Johnson company) manufactures and sells such stapling devices. Circular stapling devices manufactured by Ethicon are referred to under the trade names PROXIMATE® PPH, CDH, and ILS. Linear staplers manufactured by Ethicon under the trade names CONTOUR and PROXIMATE also can use the force switch. In each of these exemplary staplers, tissue is compressed between a staple cartridge and an anvil and, when the staples are ejected, the compressed tissue is also cut. In this specific example, the tissue can be compressed too little (where blood color is still present in the tissue, too much (where tissue is crushed), or just right (where the tissue is blanched). Staples delivered have a given length and the cartridge and anvil need to be at a given distance so that the staples close upon firing. Therefore, these staplers have devices indicating the relative distance between the two planes and whether or not this distance is within the staple length firing range. However, these staplers do not have any kind of active compression indicator that would also optimize the force acting upon the tissue that is to be stapled. The force switch described herein provides such a feature. Some exemplary procedures in which these staplers could use the force switch include colon dissection and gastric bypass surgeries.

In accordance with another feature of the invention, mechanical force switch to be disposed along a longitudinal device axis of a medical device, the switch including an electrically conductive switching piston forming a first of two electrical contacts, the piston having a longitudinal piston axis to be disposed parallel to the longitudinal device axis and a bias-device contact, a hollow body defining a body interior cavity in which the piston is movably disposed along the piston axis to define a switch-making piston position at a first longitudinal position with respect to the body and a switch-breaking piston position at a second longitudinal position with respect to the body different from the first longitudinal position, an end stop defining a second interior cavity in which the piston is movably disposed, the end stop being at least partly disposed in the body interior cavity, a bias device being disposed about at least a portion of the piston between the end stop and the bias-device contact and imparting a variable longitudinal bias thereagainst to retain the piston in one of two positions selected from the switch-making position and the switch-breaking position until an external force imparted to the piston along the longitudinal piston axis exceeds the longitudinal bias and, when the external force exceeds the longitudinal bias, the piston moves to the other of the two positions, a magnitude of the longitudinal bias being dependent upon a longitudinal position of the end stop within the body interior cavity, and an electrically conductive second contact electrically insulated from the piston and forming a second of the two electrical contacts, the first and second electrical contacts being in the switch-making state when the piston is in the switch-making position and in the switch-breaking state when the piston is in the switch-breaking position.

In accordance with a further feature of the invention, the longitudinal piston axis is to be disposed coincident with the longitudinal device axis.

In accordance with an added feature of the invention, the bias device imparts the longitudinal bias to retain the piston in the switch-breaking position to create a normally open switch configuration.

In accordance with an additional feature of the invention, the bias device imparts the longitudinal bias to retain the piston in the switch-making position to create a normally closed switch configuration.

In accordance with yet another feature of the invention, a distance between the first longitudinal position and the switch-breaking position is between approximately 25 μm and approximately 750 μm, in particular, between approximately 75 μm and approximately 200 μm.

In accordance with yet a further feature of the invention, a range of force to switch between the switch-making and switch-breaking states is between approximately 3 ounces and approximately 20 pounds, in particular, between approximately 5 pounds to approximately 8 pounds.

In accordance with yet an added feature of the invention, there is provided a switch sub-assembly having the electrically conductive second contact, a switch housing longitudinally fixedly and electrically conductively connected to the body and at least partially surrounding the second contact, a switch insulator electrically insulating the second contact from the switch housing, and a piston contact movably disposed in the housing and longitudinally fixedly and electrically conductively connected to the piston.

In accordance with yet an additional feature of the invention, the switch insulator at least partially surrounds the piston contact, the electrically conductive second contact at least partially surrounds the switch insulator, and the switch housing at least partially surrounds the second contact, the switch insulator, and the piston contact.

In accordance with again another feature of the invention, the second contact is electrically insulated from the body and the piston.

In accordance with again a further feature of the invention, the switch insulator at least partially surrounds the electrically conductive second contact and the switch housing at least partially surrounds the second contact, the switch insulator, and the piston contact.

In accordance with again an added feature of the invention, the piston has a first circular-shaped exterior, the bias-device contact has a second circular-shaped exterior having a larger diameter than the first circular-shaped exterior, the body interior cavity has a first circular-shaped interior substantially equal to the second circular-shaped exterior, the second interior cavity has a second circular-shaped interior substantially equal to the first circular-shaped exterior, the bias device has a third circular-shaped exterior substantially equal to the first circular-shaped interior, and the second contact has a fourth circular-shaped exterior smaller in diameter than the first circular-shaped interior.

In accordance with again an additional feature of the invention, the piston, the end stop and the body form an assembly selected from the group consisting of the end stop being threaded into the body interior cavity to longitudinally fix and rotationally adjust the end stop within body first interior cavity and the end stop floating about the piston and within the body.

In accordance with still another feature of the invention, there is provided an electric indication circuit electrically connected to the first and second contacts and having an indicator transmitting state-change information to a user signaling that a state change of the piston has occurred.

In accordance with still a further feature of the invention, the bias device is a compression spring compressed between the bias-device contact and the end stop around the piston to bias the piston in a direction away from the end stop.

With the objects of the invention in view, there is also provided a mechanical force switch to be disposed along a longitudinal device axis of a medical device and electrically actuating a change of state when a predefined force along the longitudinal device axis is exceeded, the switch including an electrically conductive switching piston forming a first of two electrical contacts of the switch, the piston having a longitudinal piston axis to be disposed coincident with the longitudinal device axis, a piston portion having a first exterior, and a flange having a flange exterior, and a hollow body defining a first interior cavity having a first interior substantially equal to the flange exterior, the piston being movably disposed in the first interior cavity along the longitudinal piston axis to define a switch-making piston position at a first longitudinal position with respect to the body, and a switch-breaking piston position at a second longitudinal position with respect to the body different from the first longitudinal position, an end stop defining a second interior cavity having a second interior substantially equal to the first exterior, the piston portion being movably disposed in the second interior cavity, the end stop being disposed in the first interior cavity and having a bias-device contact surface and an stop exterior substantially equal to the first interior, a bias device having a third exterior substantially equal to the first interior and being disposed about the piston portion between the bias-device contact surface and the flange, the bias device imparting a variable longitudinal bias against the flange to retain the piston in one of two positions selected from the switch-making position and the switch-breaking position until an external force imparted to the piston along the longitudinal piston axis exceeds the longitudinal bias and, when the external force exceeds the longitudinal bias, the piston moves to the other of the two positions, a magnitude of the longitudinal bias being dependent upon a longitudinal position of the end stop within the first interior cavity, and a switch assembly having a housing longitudinally connected to the hollow body, a switch sub-assembly longitudinally connected to the piston and movably disposed in the housing, the sub-assembly having a switch insulator and an electrically conductive second contact electrically insulated from the piston, the first and second contacts being in the switch-making state when the piston is in the first longitudinal position and in the switch-breaking state when the piston is in the second longitudinal position.

In accordance with still an added feature of the invention, the piston has a proximal end and the flange is at the proximal end, the end stop is threaded into the first interior cavity to longitudinally fix and rotationally adjust the end stop within the first interior cavity and the piston portion is slidably disposed in the second interior cavity.

With the objects of the invention in view, there is also provided a mechanical force switch to be disposed along a longitudinal device axis of a medical device and electrically actuating a change of state when a predefined force along a longitudinal axis of a device is exceeded, the switch including a switching piston defining an internal cavity and having a first portion having a first exterior, a second portion having a second exterior and an outer flange with an flange exterior, at least one electroconductive portion forming a first of two contacts of an electrical switch for signaling a switching state of the piston and a longitudinal piston axis to be disposed coincident with the longitudinal device axis, a hollow body defining a first interior cavity having a first interior and a second interior cavity having a second interior substantially equal to the flange exterior, the piston being movably disposed in the first and second interior cavities along the longitudinal piston axis to define a switch-making piston position at a first longitudinal position with respect to the body and a switch-breaking piston position at a second longitudinal position with respect to the body different from the first longitudinal position, at least one adjustable end stop having a stop exterior substantially equal to the first interior and defining a stop interior cavity having a stop interior substantially equal to the first exterior, a bias device having a bias exterior substantially equal to the second interior and disposed about the first portion between the end stop and the outer flange, the bias device imparting a variable longitudinal bias against the outer flange to retain the piston in one of two positions selected from the switch-making position and the switch-breaking position until an external force imparted to the piston along the longitudinal piston axis exceeds the longitudinal bias and, when the external force exceeds the longitudinal bias, the piston moves to the other of the two positions, a magnitude of the longitudinal bias being dependent upon a longitudinal position of the end stop within the first interior cavity, and a switch assembly longitudinally connected to the body and having a switch insulator and an electrically conductive second contact electrically insulated from the piston, the first and second contacts being in the switch-making state when the piston is in the first longitudinal position and in the switch-breaking state when the piston is in the second longitudinal position.

In accordance with still an additional feature of the invention, the second interior permits longitudinal sliding translation of the outer flange within the second interior cavity and the stop interior slidably receives the first portion of the piston therein.

In accordance with another feature of the invention, the piston has a proximal end and the outer flange is at the proximal end, the end stop is threaded into the first interior cavity to longitudinally fix and rotationally adjust the end stop within the first interior cavity, and the piston portion is slidably disposed in the stop interior cavity.

In accordance with a concomitant feature of the invention, the first portion is a distal portion, the second portion is a proximal portion, the first interior cavity is a distal cavity having interior threads, the second interior cavity is a proximal cavity, the first interior of the distal cavity is larger than the second interior of the proximal cavity, and the end stop has exterior threads mating with the interior threads.

Other features that are considered as characteristic for the invention are set forth in the appended claims.

Although the invention is illustrated and described herein as embodied in a force switch, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

BRIEF DESCRIPTION OF THE DRAWINGS

Advantages of embodiments the present invention will be apparent from the following detailed description of the preferred embodiments thereof, which description should be considered in conjunction with the accompanying drawings in which.

DETAILED DESCRIPTION OF THE PREFERRED EMBODIMENTS

Figure 1:
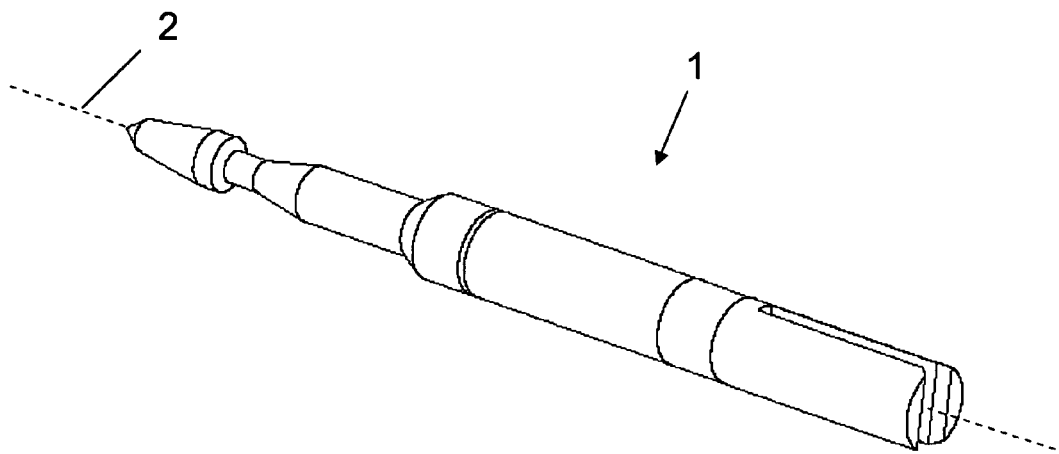
FIG. 1 is a perspective view from a side of an exemplary embodiment of a force switch according to the invention.
Figure 2:
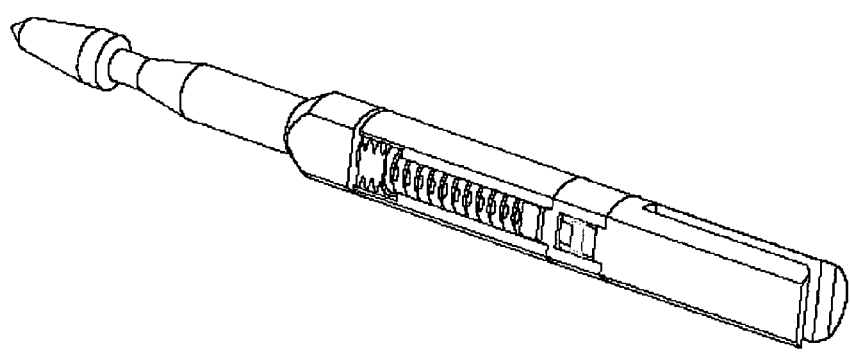
FIG. 2 is a longitudinally cross-sectional perspective view from a side of the force switch of FIG. 1 through a near half of the switch.
Figure 3:
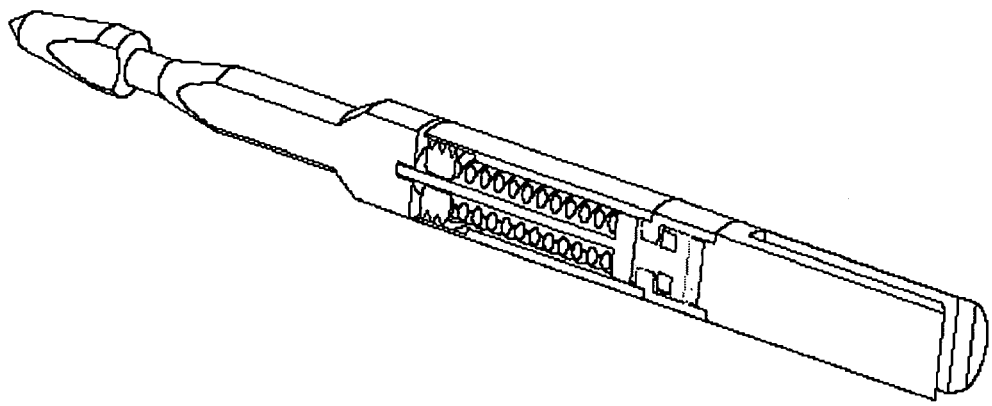
FIG. 3 is a longitudinally cross-sectional perspective view from a side of the force switch of FIG. 1 through a near half of the switch.
Figure 4:
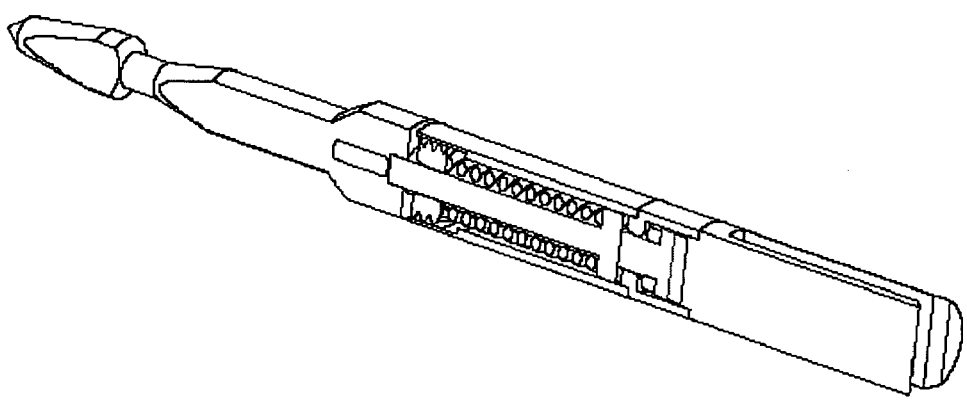
FIG. 4 is a longitudinally cross-sectional perspective view from a side of the force switch of FIG. 1 through a near half of the switch.
Figure 5:
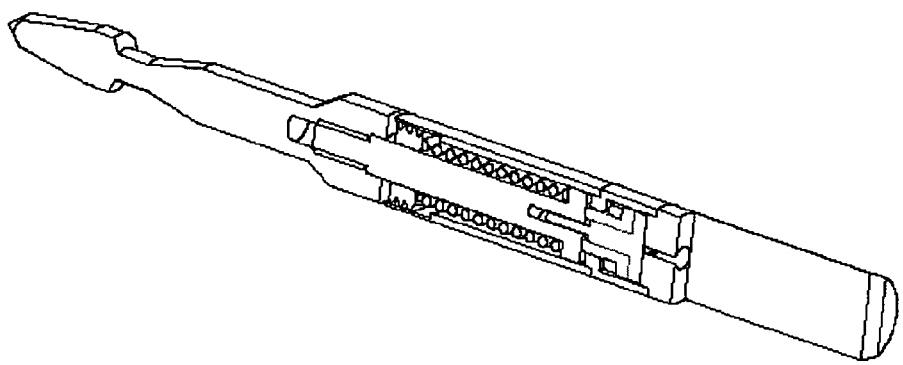
FIG. 5 is a longitudinally cross-sectional perspective view from a side of the force switch of FIG. 1 through a near half of the switch.

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention.

Before the present invention is disclosed and described, it is to be understood that the terminology used herein is for the purpose of describing particular embodiments only and is not intended to be limiting. It must be noted that, as used in the specification and the appended claims, the singular forms "a," "an," and "the" include plural references unless the context clearly dictates otherwise.

While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Referring now to the figures of the drawings in detail and first, particularly to FIGS. 1 to 9 thereof, there is shown a first exemplary embodiment of a force switch 1. FIGS. 10 to 17 illustrate a second exemplary embodiment of the force switch 1. As will be described in more detail below, the first exemplary embodiment represents a "normally open" switch configuration and the second exemplary embodiment represents a "normally closed" switch configuration. Where features of the switch 1 are similar in the two embodiments, for ease of understanding, similar reference numerals will be used.

Figure 6:
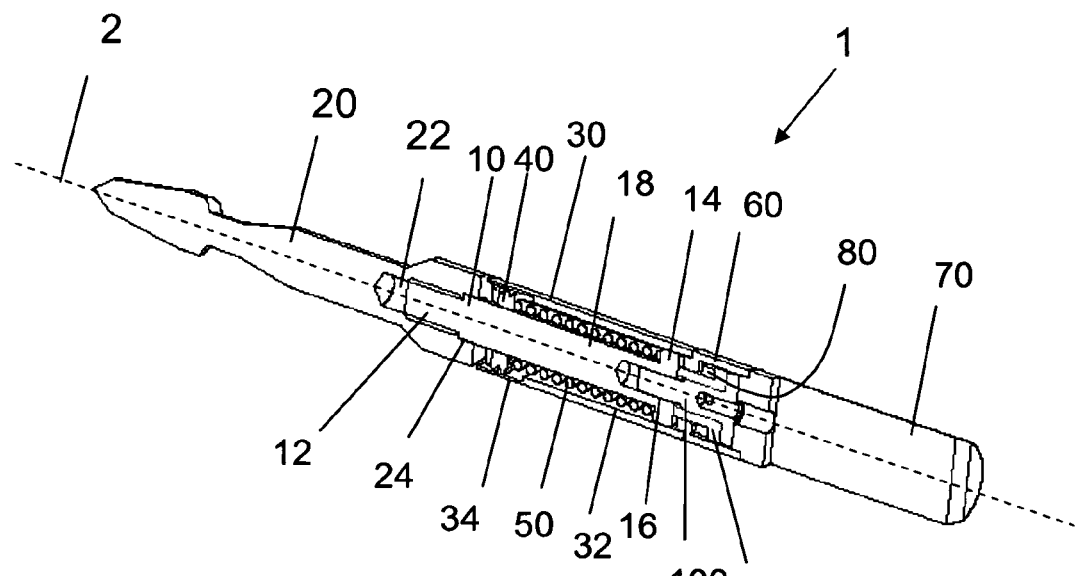
FIG. 6 is a longitudinally cross-sectional perspective view from a side of the force switch of FIG. 1 through approximately a longitudinal axis of the switch.

The force switch 1 can be incorporated into a device where force along the longitudinal axis of the device needs to be measured and an action needs to be taken when that force exceeds a given predetermined value. This force switch 1 can be used, for example, in a medical device, but is not limited to the exemplary embodiment of a medical device. As will be described in further detail below, the force switch 1 can be used with a circular surgical stapling device such as is disclosed in U.S. Pat. No. 5,104,025 to Main FIGS. 1 to 9 represent different portions of the force switch 1. FIG. 6 provides an example view through the longitudinal axis 2 of the force switch 1 that allows one to see all parts of the switch 1. A contact piston 10 provides a central part around which other parts of the switch 1 may be explained. A nose piece or tip 20 is fastened to the distal end 12 of the contact piston 10. The distal end 12 and an internal bore 22 of the tip 20 are illustrated with straight lines in FIGS. 4 to 9, however, in a first exemplary embodiment, the distal end 12 can be provided with external male threads and the bore 22 can be provided with internal female threads. Alternatively, the tip 20 can be press-fit, glued, welded, or otherwise connected to the distal end 12 of the contact piston 10. In the configuration shown in FIGS. 4 to 9, a proximal portion 24 of the internal bore 22 has a non-threaded flat portion for receiving therein the distal-most end of the piston 10 such that, when completely threaded into the bore 22, the proximal portion 24 acts as a stop for further threading of the distal end 12 therein.

At the proximal end of the piston 10, a widening 14 is provided on the outside surface of the piston 10 and an internal bore 16 is formed in the interior thereof.

A hollow body tube 30 is disposed around at least a portion of the contact piston 10. One exemplary embodiment of the interior of the tube 30 includes a relatively narrower proximal bore 32 and a relatively wider distal bore 34 (although the opposite configuration is also possible). The bores 32, 34 surround a proximal portion of the piston 10 that includes a central shaft 18 thereof and the widening 14. The exterior shape of the widening 14 and the interior shape of the proximal bore 32 are substantially equal. Accordingly, in a circular configuration, the interior diameter of the proximal bore 32 is substantially equal to the outer diameter of the widening 14. As used herein, substantially equal means that there is only a sufficient clearance between the two parts to allow one to slide within the other. Thus, if a given first material requires a particular first spacing between the outer surface of the piston 10 and the inner surface of the body tube 30 to permit the piston 10 to move therein, then that first spacing exists between the two parts 10, 30, whereas, if a given second material requires a smaller (or larger) spacing between the outer surface of the piston 10 and the inner surface of the body tube 30 to permit the piston 10 to move therein, then that second spacing exists between the two parts 10, 30.

There are two parts between the piston 10 and the body tube 30, an adjustable end cap 40 and a bias device 50. The exterior shape of the end cap 40 and the interior shape of the distal bore 34 are substantially equal. Accordingly, in a circular configuration, the interior diameter of the distal bore 34 is substantially equal to the outer diameter of the end cap 40. Thus, when the end cap 40 is inserted into the distal bore 34, the cap 40 substantially closes an interior space defined by the interior surfaces of the distal and proximal bores 34, 32, the exterior surface of the central shaft 18, the distal transverse surface of the widening 14, and the proximal end surface of the cap 40. The bias device 50 is disposed inside this interior space. The bias device 50 and the cap 40 act together with the widening 14 to bias the piston 10 in a given direction, in this case, in the proximal direction. Force of the bias device 50 can be dependent upon the position of the cap 40. For example, if the cap 40 is closer to the widening 14, the bias device 50 can exert a first biasing force and if the cap 40 is further from the widening 14, the bias device 50 can exert a second biasing force. Depending upon the bias device 50 used, the first force can be greater than the second, or vice-versa. It is beneficial, but not required, if the cap 40 is adjustable between various locations along the body tube 30. In such a configuration, the bias device 50 can be adjusted to a user-desired pre-bias.

One embodiment of the cap 40 and bias device 50 is shown in FIGS. 2 to 9. The following description, however, will be directed to the view of FIG. 8. In this embodiment, the distal bore 34 has a larger diameter than the proximal bore 32. The end cap 40 has exterior threads 42 that mate with non-illustrated internal female threads of the distal bore 34. In such a configuration, the cap 40 can be rotated into the distal bore 34 along any longitudinal point within the distal bore 34. With the proximal bore 32 having a smaller diameter than the distal bore 34, the distal endpoint 36 of proximal bore 32 forms a stop for insertion of the cap 40. The cap 40 is formed with an interior bore 44 having a shape substantially equal to the outer shape of the central shaft 18 of the piston 10. Thus, while the cap 40 can be screwed into the distal bore 34 such that longitudinal forces will not press the cap 40 out from the distal bore 34, the central shaft 18 of the piston 10 can move longitudinally freely within the bore 44 and with respect to the cap 40.

The bias device 50 is embodied, in this example, as a compression spring 50. As such, when the spring 50 is placed around the central shaft 18 of the piston 10 up to the distal transverse surface of the widening 14, and when the threaded cap 40 is also placed around the central shaft 18 and screwed at least partially within the distal bore 34, the spring 50 can be compressed between two extremes defined by the longitudinal connection distance that the cap 40 can traverse between being securely but barely inside the distal bore 34 and fully inserted therein up to the stop 36.

Because the piston 10 moves, it can form one contact of an electrical switch for signaling a state of the piston 10. Another contact needs to be provided that is electrically insulated from the piston 10. Thus, the piston 10 needs to be associated with a switch sub-assembly so that the electrical switch is in a first state when the piston 10 is in a first longitudinal position and in a second state when the piston 10 is in a second longitudinal position (the first and second states being off/on or on/off). This switch sub-assembly is formed at a proximal end of the piston 10 and the body tube 30 and, in the following text, is shown in two exemplary embodiments. The first embodiment, the "normally open" switch has been mentioned as being related to FIGS. 1 to 9. The second embodiment relates to FIGS. 10 to 17 and is a "normally closed" switch.

Figure 8:
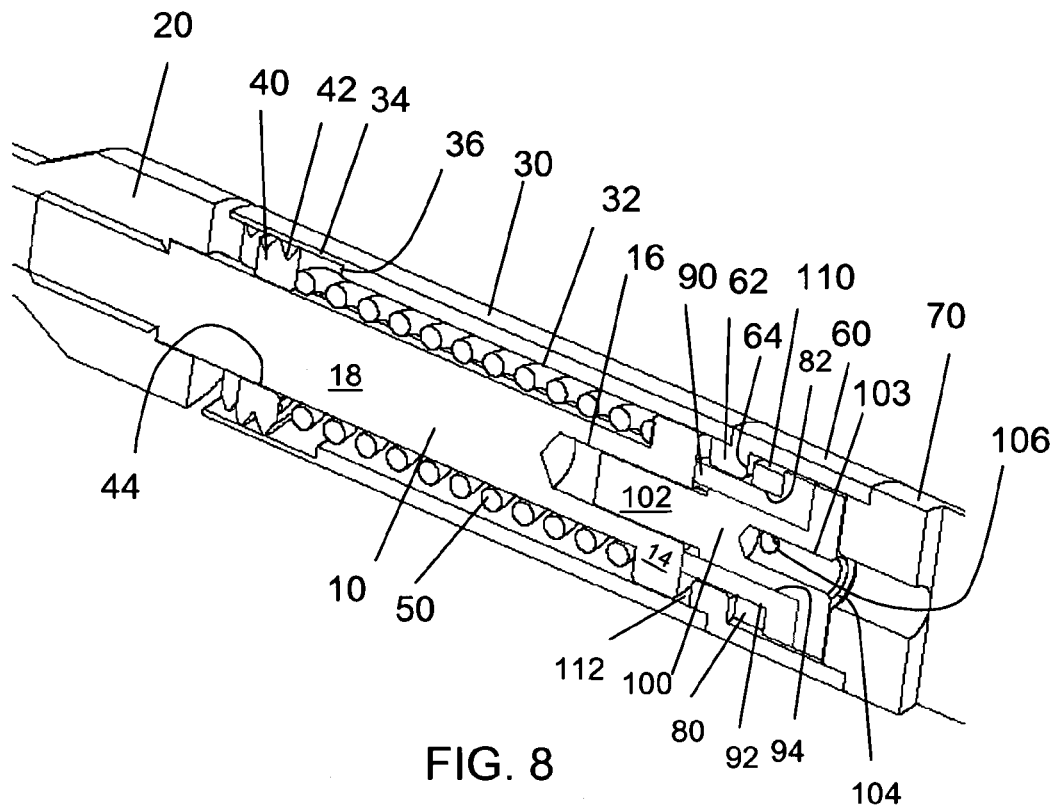
FIG. 8 is an enlarged, longitudinally cross-sectional perspective view from a side of the force switch of FIG. 6 with the switch in an un-actuated position.
Figure 9:
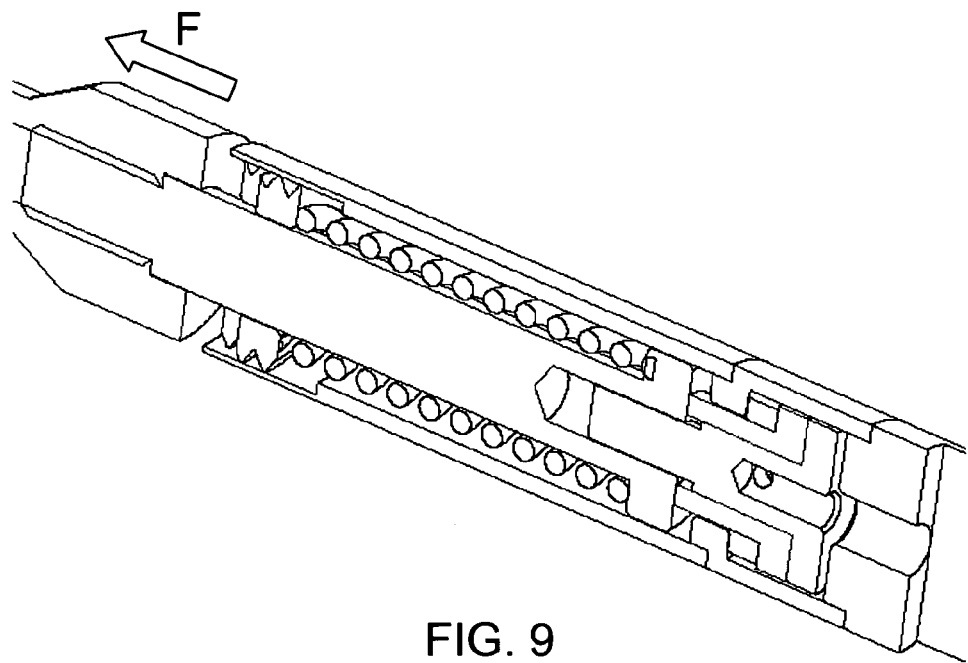
FIG. 9 is an enlarged, longitudinally cross-sectional perspective view from a side of the force switch of FIG. 6 with the switch in an actuated position.

The normally open switch sub-assembly is explained with regard to FIGS. 8 to 9. A switch bushing 60 has a distally projecting stub 62 that is inserted into the proximal end of the body tube 30. This stub 62 can be connected to the body tube 30 in any number of ways (e.g., by bonding, welding, adhesive, press-fit, screw threads). The proximal end of the switch bushing 60 is attached to a mounting body 70. In one embodiment, each of the piston 10, the tip 20, the body tube 30, the cap 40, the switch bushing 60, and the mounting body 70 are electrically conductive and provide a first electrical contact of the force switch 1. However, the tip 20 and cap 40 need not be conductive. To form a second electrical contact that, when put into electrical connection with the first contact, completes an electrical circuit (or interrupts an electrical circuit as shown in FIGS. 10 to 17), an insulating body needs to be disposed between the second contact and the first contact needs to be operatively moved into (or out of) contact with the second contact.

Various switch embodiments disclosed herein include parts that are electrically conductive and actually form part of the electronic circuit. The switch according to the present invention, however, is not limited to embodiments where parts of the switch form the circuit. An alternative configuration can take advantage only of the mechanical switch-breaking aspects of the invention to have the movement of the piston actuate a separate electrical switch adjacent the switch, e.g., the piston. Such an external switch can be embodied as what is referred to in the art as a tact switch because such a switch is very small. Various microswitches can be used as well if there is sufficient room for such larger switches.

In the exemplary embodiment of FIGS. 1 to 9, the second electrical contact is formed by a contact ring 80 and the insulating body is formed by an insulating stub 90. The part that connects the ring 80 and the insulating stub 90 to the piston 10 is a T-shaped connecting bar 100. Each of the ring 80, the stub 90, and the bar 100 are nested in their shape so that they can fit in an easy assembly into the switch bushing and the body tube 30. The insulating stub separates the contact ring 80 from the connecting bar 100, which is in electrically conductive contact with the piston 10 and the switch bushing 60.

More specifically, the internal bore 16 is shaped to receive a distal boss 102 of the connecting bar 100. The connection between the distal boss 102 and the internal bore 16 can be like any of the embodiments of the connection between the piston 10 and the tip 10. If the boss 102 has an external male thread, for example, then the internal bore 16 has a corresponding female internal thread. Such an exemplary configuration makes attachment of the connecting bar 100 and the piston 10 easy with regard to manufacturing costs and time.

The contact ring 80 has an internal bore 82 having a shape dimensioned to correspond substantially to the outer shape of a distal contact portion 92 of the insulating stub 90. This external outer shape of the distal contact portion 92 can take any polygonal shape, such as circular, ovular, rectangular, square, star, triangular, for example. Regardless of this outer shape, the shape of the internal bore of the contact ring 80 corresponds thereto so that the contact ring 80 can be inserted thereon and fixed (whether by press-fit, adhesive, bonding, welding, or any other connection process) thereto so that control of contact between the ring 80 and any other portion of the first contact can be made with high precision.

After the contact ring 80 is connected to the insulator stub 90, the combined assembly can be connected to the connecting rod 100. The external shape of an intermediate portion of the rod 100 is made to correspond to an internal shape of a bore 94 extending through the insulator stub 90. Again, the outer shape of the intermediate portion of the rod 100 can take any polygonal shape, such as circular, ovular, rectangular, square, star, triangular, for example. Regardless of this outer shape, the shape of the internal bore of the insulator stub 90 corresponds thereto so that the insulator stub 90 can be inserted thereon and fixed (whether by press-fit, adhesive, bonding, welding, or any other connection process) thereto so that control of contact between the ring 80, mounted to the stub 90, and any other portion of the first contact can be made with high precision.

With such a connection, the connecting rod 100 electrically contacts the piston 10 (and, thereby, the tip 20, the body tube 30, the cap 40, the switch bushing 60, and the mounting body 70). The outer shape/diameter of the contact ring 80 is dimensioned to be smaller than the inner shape/diameter of the switch bushing 60 and insertion of the contact ring 80 inside the switch bushing 60 creates a transverse gap 110 therebetween. Thus, the contact ring 80 is electrically isolated from the switch bushing 60 on the outer side thereof by the transverse gap 110 and is electrically isolated (insulated) from the connecting rod 100 on the inner side thereof by being in direct contact with the outside surface of the insulator stub 90.

To make an electric circuit including the contact ring 80 and any electrically conducting part of the first contact (10, 20, 30, 40, 60, 70), an electrical connection must be made at the contact ring 80. One exemplary embodiment for such a connection is illustrated in FIGS. 5 to 9. Specifically, the connecting bar 100 is formed with the proximal longitudinal bore 103 extending from the proximal transverse exterior surface 104 up to and including at least a part of the intermediate portion the connecting rod 100 that is located at a longitudinal position where the contact ring 80 is disposed. A further transverse bore 106 is formed to connect the longitudinal bore 103 with an interior surface of the contact ring 80. In such a configuration, an insulated wire 206 can be threaded through the longitudinal 103 and transverse 104 bores and fastened (e.g., by welding) to the interior surface of the contact ring 80. For ease of such a connection, the contact ring 80 can be formed with a depression (or a series of depressions) on the inside surface for receiving the electrical portion of the wire while the insulating portion of the wire remains in contact with the entirety of the longitudinal 103 and transverse 104 bores of the connecting rod 100.

Figure 7:
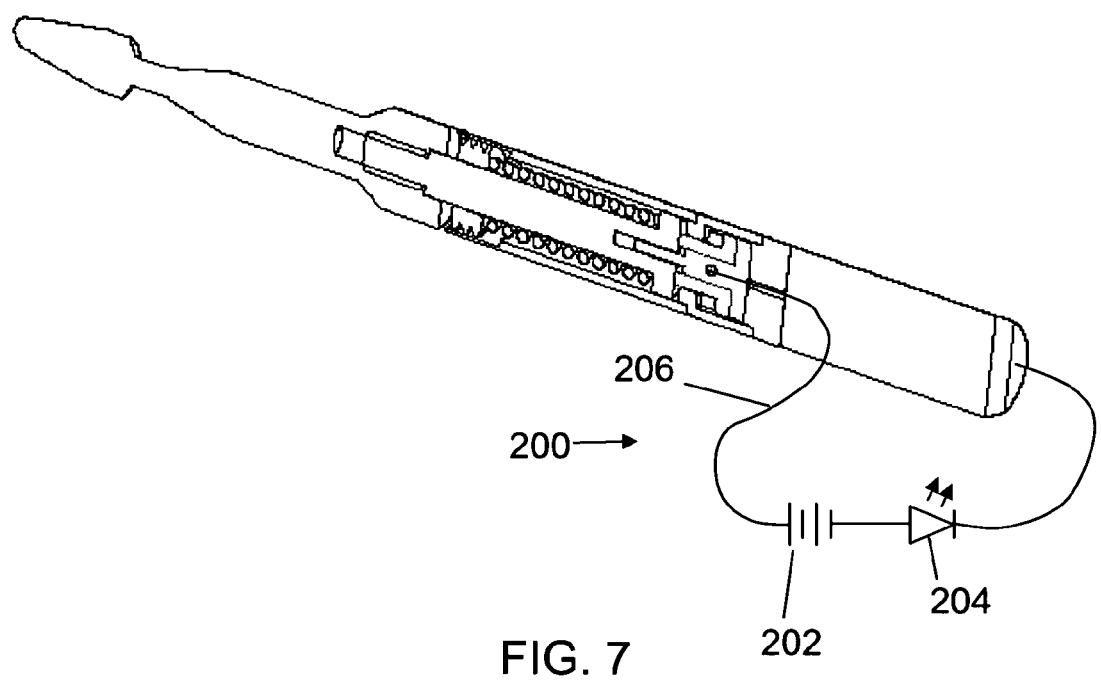
FIG. 7 is a longitudinally cross-sectional perspective view from a side of the force switch of FIG. 1 through a far half of the switch.

Such an electrical connection is, for example diagrammatically shown in FIG. 7, where circuitry 200 is disposed between the contact ring 80 and the mounting body 70. This exemplary circuitry includes a power source 202 and a contact indicator 204 (i.e., an LED) that lights the LED when the electrical circuit is completed. If the mounting body 70 and the insulated wire 206 are each connected to the circuitry 200 (as shown in FIG. 7), then, when electrical contact occurs between the contact ring 80 and any part of the first contact (10, 20, 30, 40, 60, 70), the LED 204 will illuminate.

With the above exemplary configuration set forth, the functioning of the switch 1 between the first and second states can be described with regard to a comparison between FIGS. 8 and 9. The piston 10 is longitudinally fixed to the tip 20 and to the connecting rod 100. Further, the insulator stub 90 and the contact ring 80 are longitudinally fixed to the exterior of the connecting rod 100. The piston 10 is slidably disposed inside the bore 44 of the cap 40 at the distal end and is slidably disposed inside the proximal bore 32 of the tube body 30. Thus, the entire piston sub-assembly (10, 20, 80, 90, 100) can move in a longitudinal direction because a longitudinal gap 112 exists between the distal transverse surface of the contact ring 80 and a proximal end surface 64 of the stub 62 of the switch bushing 60. It is this gap 112 that forms the space over which the force switch 1 can function.

The bias device (e.g., compression spring) 50 disposed between the adjustable cap 40 and the distal transverse surface of the widening 14 imparts a proximally directed force against the piston 10 when the cap 40 is adjusted to compress the spring 50. This force, referred to herein as a pre-tension, keeps the contact ring 80 at a distance from the electrically conductive stub 62 of the switch bushing 60—which is defined as the longitudinal gap 112. Without any external force imparted on the force switch 1, the pre-tension will always keep the contact ring 80 at this position and electrical contact between the first contact and the contact ring 80 will not occur. A distally directed external force F imparted upon the tip 20 could alter this situation. See FIG. 9. If the force F is not as great as the pre-tension force imparted by the spring 50, then the spring will not compress any further than it has already been compressed by the adjustable cap 40. However, if the force F is greater than the pre-tension force imparted by the spring 50, then the spring will compress and the tip 20 along with the remainder of the piston sub-assembly—the piston 10, the connecting rod 100, the insulating stub 90, and the contact ring 80—will move in a distal longitudinal direction. The distal longitudinal direction is limited by the proximal end surface 64 of the stub 62 of the switch bushing 60 because contact between the end surface 64 and the distal side of the contact ring 80 completely prevents further movement of the tip 20. This configuration, therefore, provides an electrical switch that has an adjustable longitudinal pre-tension force that must be overcome before the switch 1 can actuate and complete the electrical circuit that is "open" until the contact ring 80 touches the switch bushing 60. FIG. 9 shows the piston sub-assembly (10, 20, 80, 90, 100) in the actuated distal position and FIG. 8 shows the piston sub-assembly in the un-actuated proximal position One exemplary process for assembly of the force switch 1 of FIGS. 1 to 9, has the spring 50 inserted over the central shaft 16 of the piston 10. The cap 40 is also screwed into the proximal bore 34 of the body tube 30. The piston-spring sub-assembly is, then inserted through the interior bore 44 of the cap 40 and the tip 20 is fastened (e.g., screwed) onto the distal end 12 of the piston 10. This forms a piston sub-assembly.

The insulating stub 90 is attached to the intermediate portion of the connecting bar 100 by being placed, first, over the distal boss 102 and, second, over the intermediate portion. Similarly, the contact ring 80 is attached to the insulating stub 90 by being placed thereover. The ring 80 is longitudinally connected to the insulating stub 90 and the stub 90 is longitudinally connected to the intermediate portion of the connecting bar 100. The insulated wire 206 is passed through the bore of the mounting body 70 and through both the longitudinal 103 and transverse 106 bores of the connecting rod 100 and electrically connected to the interior surface of the contact ring 80 without electrically connecting the wire 206 to any portion of the mounting body 70 or the connecting bar 100. This connection forms a switch sub-assembly that is ready to be connected to the piston sub-assembly.

Either or both of the distal boss 102 of the connecting bar 100 or the stub 62 of the switch bushing 60 can have threads for connecting the boss 102 to the piston 10 and/or the stub 62 to the body tube 30. As such, the entire switch sub-assembly can be connected (both physically and electrically) to the piston sub-assembly. With these two sub-assemblies connected together, only the mounting body 70 needs to be connected to the proximal end of the switch bushing 60. Such a connection can take any form, for example, the connection can be a weld or a mated set of screw threads.

FIGS. 10 to 17 illustrate a second exemplary embodiment of the force switch 1 having a "normally closed" switch configuration.

Figure 13:
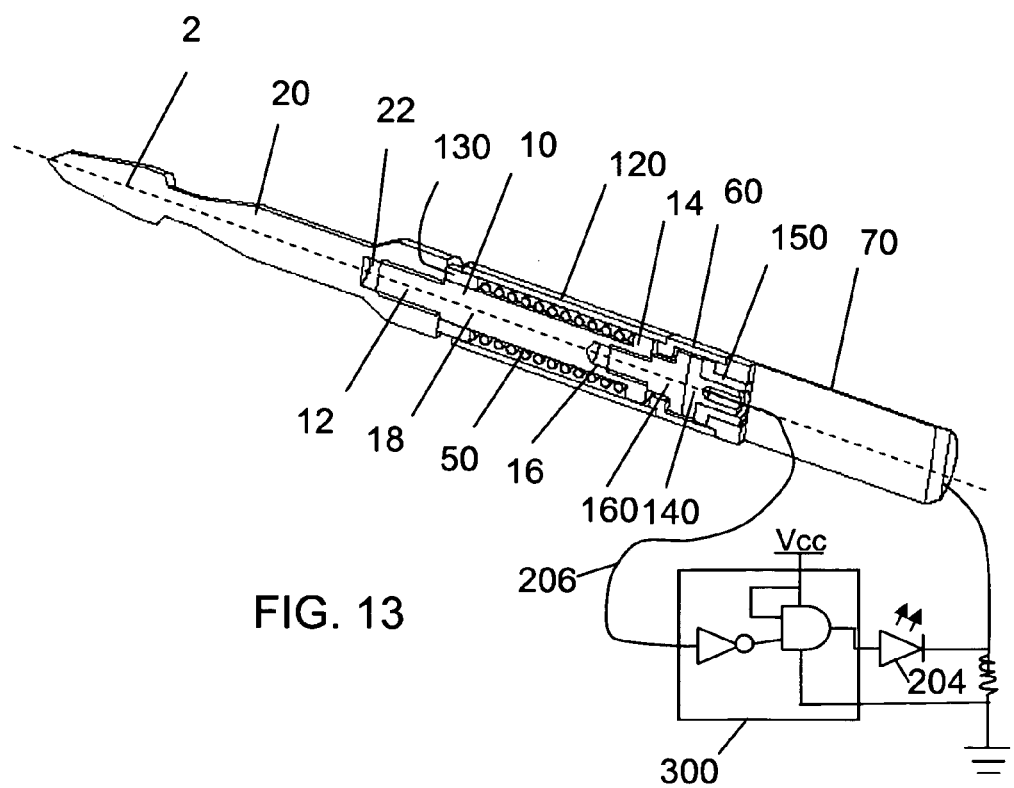
FIG. 13 is a longitudinally cross-sectional perspective view from a side of the force switch of FIG. 10 through approximately a longitudinal axis of the switch.
Figure 14:
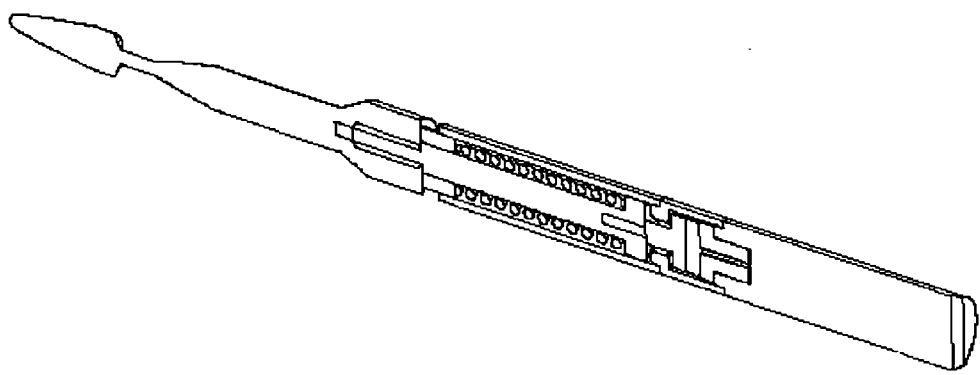
FIG. 14 is a longitudinally cross-sectional perspective view from a side of the force switch of FIG. 10 through a far half of the switch.
Figure 15:
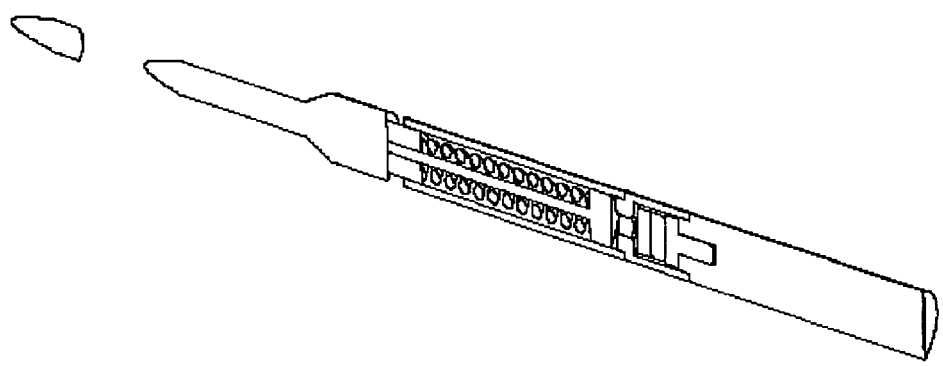
FIG. 15 is a longitudinally cross-sectional perspective view from a side of the force switch of FIG. 10 through a far half of the switch.

FIGS. 10 to 17 illustrate different portions of the force switch 1. FIG. 14 provides an example view approximately through the longitudinal axis 2 of the force switch 1 that allows visualization of all parts of the switch 1. The contact piston 10 provides a central part around which other parts of the switch 1 may be explained. The tip 20 is fastened to the distal end 12 of the contact piston 10. The distal end 12 and the internal bore 22 of the tip 20 are illustrated with straight lines in FIGS. 13 to 15 and 17, however, in the exemplary embodiment, the distal end 12 can be provided with external male threads and the bore 22 can be provided with internal female threads. Alternatively, the tip 20 can be press-fit, glued, welded, or otherwise connected to the distal end 12 of the contact piston 10. In the configuration shown in FIGS. 13 to 15 and 17, the proximal portion 24 of the internal bore 22 has the non-threaded flat portion for receiving therein the distal-most end of the piston 10 such that, when completely threaded into the bore 22, the proximal portion 24 acts as a stop for further threading of the distal end 12 therein.

The piston 10 has a proximal end at which the widening 14 is provided to extend radially the outside surface of the piston 10. The internal bore 16 is formed in the interior of the piston 10 at the proximal end.

Figures 16, 17:
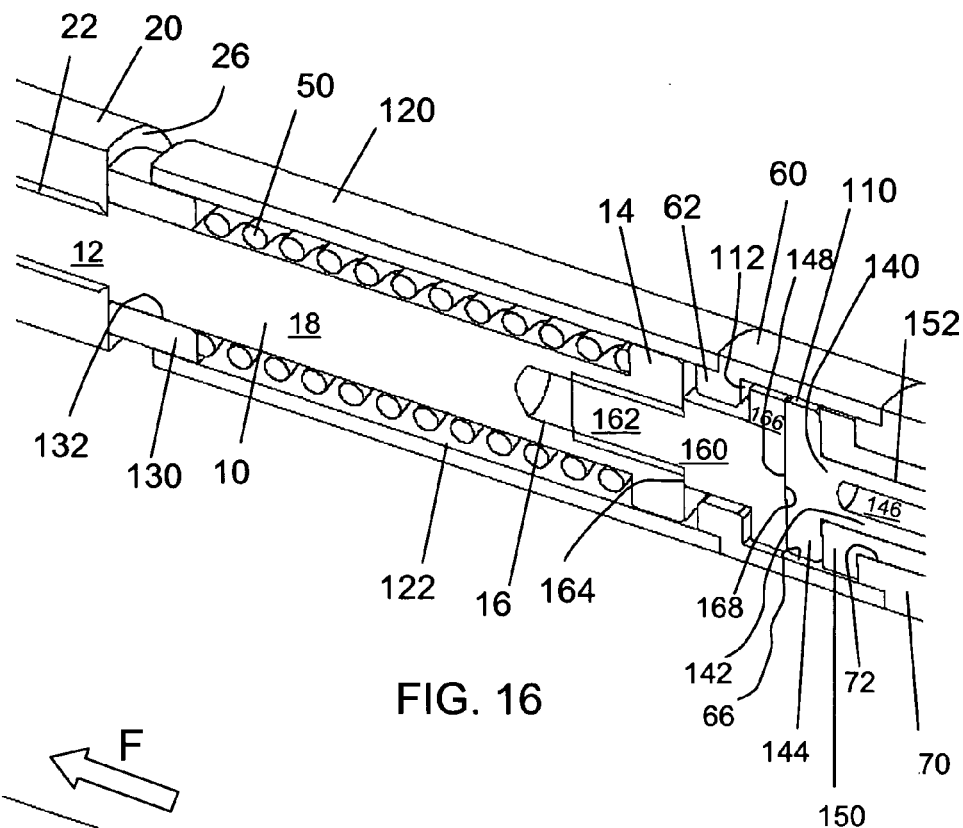
FIG. 16 is an enlarged, longitudinally cross-sectional perspective view from a side of the force switch of FIG. 13 with the switch in an un-actuated position.
FIG. 17 is an enlarged, longitudinally cross-sectional perspective view from a side of the force switch of FIG. 13 with the switch in an actuated position.

As shown in the enlarged view of FIG. 16, a hollow body tube 120 is disposed around at least a portion of the contact piston 10. As compared to the first embodiment of the body tube 30, the interior of this tube 120 has a constant diameter bore 122. The bore 122 has a shape substantially equal to an exterior shape of the widening 14 and surrounds the central shaft 18 of the piston 10. Accordingly, in a circular configuration, the interior diameter of the bore 122 is substantially equal to the outer diameter of the widening 14.

There are two parts of the force switch 1 disposed between the piston 10 and the body tube 120: a spring stop puck 130 and a bias device 50. The exterior shape of the spring stop puck 130 and the interior shape of the bore 122 are substantially equal. Accordingly, in a circular configuration, the interior diameter of the bore 122 is substantially equal to the outer diameter of the spring stop puck 130 so that the spring stop puck 130 slides within the bore 122 substantially without play but also without substantial friction. This spring stop puck 130 differs from the end cap 40 in that it floats entirely separate within the body tube 120. More specifically, as the tip 20 is threaded onto the distal end 12 of the piston 10, the proximal transverse surface pushes against but is not fixed to the distal transverse surface of the puck 130. In such a configuration, it would, at first glance, seem to indicate that the compression spring 50 could only be set to one given compression value because the puck 130 has a fixed longitudinal length. This would be correct except a set of pucks 130 are provided, each having different longitudinal lengths. Therefore, the pre-tensioning of the spring 50 is adjusted by selecting one of the set of pucks 130. Also, it is not necessary to thread the tip 20 entirely onto the distal end 12 of the piston 10 as shown in FIG. 13, for example. Thus, if the tip 20 is not entirely threaded on the piston 10, user-desired pre-tensioning of the bias device 50 occurs by providing a specifically sized puck 130 and threading the tip 20 onto the piston 10 at a predefined distance. Alternatively, the puck 130 can solely determine the pre-tension if the tip 20 is entirely threaded onto to the piston 10. One embodiment of the stop puck 130 and bias device 50 is shown in FIGS. 10 to 17. The following description, however, is directed to the view of FIG. 13. The stop puck 130 is formed with an internal bore 132 having a shape substantially equal to the outer shape of the piston 10 so that the piston 10 can traverse through the puck 130 without hindrance.

When the spring stop puck 130 is within the bore 122, the stop puck 130 substantially closes an interior space defined by the interior surfaces of the bore 122, the exterior surface of the central shaft 18, the distal transverse surface of the widening 14, and the proximal transverse surface of the puck 130. The bias device 50 is disposed inside this interior space. The bias device 50 and the stop puck 130 act together with the widening 14 to bias the piston 10 in a given direction, in this case, in the proximal direction. Force of the bias device 50 is dependent upon the longitudinal length of the stop puck 130.

The bias device 50 is embodied, in this example, as a compression spring 50. As such, when the spring 50 is placed around the central shaft 18 of the piston 10 up to the distal transverse surface of the widening 14, and when the stop puck 130 is also around the central shaft 18 and the tip 20 is attached to the piston 10, the spring 50 is compressed or pre-tensioned therebetween.

Because the piston 10 moves, it can form one contact of an electrical switch for signaling a state of the force switch 1. Another contact needs to be provided that is electrically insulated from the piston 10. Thus, the piston 10 needs to be associated with a switch sub-assembly so that the electrical force switch 1 is in a first state when the piston 10 is in a first longitudinal position and in a second state when the piston 10 is in a second longitudinal position (the first and second states being off/on or on/off). This switch sub-assembly is formed at a proximal end of the piston 10 and the body tube 120 and, in the following text, applies to the second exemplary "normally closed" embodiment.

The switch bushing 60 has a distally projecting stub 62 that is inserted into the proximal end of the body tube 120. This stub 62 can be connected to the body tube 120 in any number of ways (e.g., by bonding, welding, adhesive, press-fit, screw threads). The proximal end of the switch bushing 60 is attached to a mounting body 70. In one embodiment, each of the piston 10, the tip 20, the body tube 120, the stop puck 130, the switch bushing 60, and the mounting body 70 are electrically conductive and provide a first electrical contact of the force switch 1. However, the tip 20 and stop puck 130 need not be electrically conductive. To form a second electrical contact that, when put into electrical connection with the first contact, interrupts an electrical circuit as shown in FIGS. 10 to 17, an insulating body needs to be disposed between the second contact and the first contact needs to be operatively moved out of contact with the second contact.

In the exemplary embodiment of FIGS. 10 to 17, the second electrical contact is formed by a contact pin 140 and the insulating body is formed by an insulating bushing 150. The part that connects the insulating bushing 150 and the contact pin 140 to the piston 10 is a T-shaped, electrically conductive, contact screw 160. The insulating bushing 150 and the contact pin 140 are nested in their shape so that they can fit in an easy assembly into the switch bushing 60 and the mounting body 70. The insulating bushing 150 physically and electrically separates the contact pin 140 from the mounting body 70 and the switch bushing 60, which is in electrically conductive contact with at least the piston 10 and the switch bushing 60.

More specifically, the internal bore 16 is shaped to receive a distal boss 162 of the contact screw 160. The connection between the distal boss 162 and the internal bore 16 can be like any of the embodiments of the connection between the piston 10 and the tip 10. If the boss 162 has an external male thread, for example, then the internal bore 16 has a corresponding female internal thread. Such an exemplary configuration makes attachment of the contact screw 160 and the piston 10 easy with regard to manufacturing costs and time. A transverse end surface 164 of the contact screw 160 also provides a stop for indicating complete insertion of the distal boss 162 inside the internal bore 16 of the piston 10.

The insulating bushing 150 has an internal bore 152 having a shape dimensioned to correspond substantially to the outer shape of a proximal contact portion 142 of the contact pin 140. This external outer shape of the proximal contact portion 142 can take any polygonal shape, such as circular, ovular, rectangular, square, star, triangular, for example. Regardless of this outer shape, the shape of the internal bore 152 of the insulating bushing 150 corresponds thereto so that the insulating bushing 150 can be inserted thereon and fixed thereto (whether by press-fit, adhesive, bonding, welding, or any other connection process) so that control of contact between the contact pin 140 and any other portion of the first contact can be made with high precision.

After the insulating bushing 150 is connected to the contact pin 140, the combined insulating sub-assembly can be connected to the mounting body 70. The external shape of a proximal portion of the insulating bushing 150 is made to correspond to an internal shape of an internal bore 72 extending through the mounting body 70. Again, the outer shape of the proximal portion of the insulating bushing 150 can take any polygonal shape, such as circular, ovular, rectangular, square, star, triangular, for example. Regardless of this outer shape, the shape of the internal bore of the mounting body 70 corresponds thereto so that the insulating bushing 150 can be inserted thereon and fixed thereto (whether by press-fit, adhesive, bonding, welding, or any other connection process) so that control of contact between the contact pin 140 (mounted in the insulating bushing 150 and the mounting body 70) and any other portion of the first contact can be made with high precision.

With such a connection, the contact screw 160 electrically contacts the piston 10 (and, thereby, the body tube 120, the switch bushing 60, and the mounting body 70, and possibly even the tip 20 and the stop puck 130 if desired). The outer shape/diameter of a distal transverse widening 144 of the contact pin 140 is dimensioned to be smaller than the inner shape/diameter of the switch bushing 60 and insertion of the contact pin 140 inside the switch bushing 60 creates a transverse gap 110 therebetween. Thus, the transverse gap 110 electrically isolates the distal widening 144 of the contact pin 140 from the inside of the switch bushing 60, and the proximal contact portion 142 of the contact pin 140 is electrically isolated (insulated) from the mounting body 70 and the switch bushing 60 on the outer side thereof by being in direct contact with the interior bore 152 of the insulating bushing 150.

To make an electric circuit between the contact pin 140 and any electrically conducting part of the first contact (e.g., 10, 20, 60, 70, 120, 130), an electrical connection must be made at the contact pin 140. One exemplary embodiment for such a connection is illustrated in FIGS. 11 to 17. Specifically, the contact screw 160 is formed with a proximal transverse widening 166 extending radially from the intermediate portion thereof and defines a proximal transverse surface 168. The bias device 50 biases the piston 10 and, thereby, the contact screw 160 in a proximal direction to electrically conductively contact the distal transverse surface 148 of the contact pin 140 to the proximal transverse surface 168 of the contact screw 160. Because such contact needs to only be made between these two surfaces to complete an electrical circuit of the switch sub-assembly, the outer shape/diameter of the proximal widening 166 of the contact screw 160 can be any size or shape that slides within the interior bore 66 of the switch bearing 60.

The other electrical contact of the contact pin 140 resides on the proximal side of the contact pin 140. In one exemplary embodiment, a longitudinal bore 146 is formed from the proximal transverse surface of the contact pin 140 inward and receives therein an insulated wire 206. The conductor of this wire 206 can be fastened (e.g., by welding) to the interior surface of the longitudinal bore 146. Such an electrical connection is, for example diagrammatically shown in FIG. 7. In such an exemplary configuration, the power source 202 supplies power to the contact indicator 204 (LED) and lights the LED when the electrical circuit is completed, which will always be the case in this normally closed configuration of the force switch 1. Conversely, when electrical contact between the first contact and the contact pin 140 is removed, the LED 104 will turn off. Of course, the indicator need not be visual (e.g., the LED 104). It can also be audible (e.g., speaker with sound) or tactile (e.g., vibration), or any combination thereof.

It is also possible to provide circuitry 300 between the contact pin 140 and the mounting body 70 that lights the LED 204 only when the electrical circuit is opened (i.e., not completed). Any logic circuitry can be used to control the LED 204 based upon the two states of the force switch 1 shown in FIGS. 10 to 17. For example, the logic 300 including a NOR gate and an AND gate can be connected to the force switch 1 circuit as shown in FIG. 13. In such a configuration, when the switch 1 is in its normally closed state, the LED is off and when contact is broken, as shown in FIG. 17, the LED will illuminate.

With the above exemplary configuration set forth, the functioning of the switch 1 between the first and second states can be described with regard to a comparison between FIGS. 16 and 17.

As set forth above, the contact pin 140 is longitudinally secured within the insulating bushing 150 and the insulating bushing 150 is longitudinally secured within at least one of the switch bearing 60 and the mounting body 70. The body tube 120 is longitudinally secured to the distal end of the switch bearing 60. The stop puck 130 is disposed, freely longitudinally, between the spring 50 and the tip 20. The piston 10 is longitudinally fixed to the tip 20 and to the contact screw 160 and this piston sub-assembly slides within the body 120 biased in the proximal direction by the spring 50. Accordingly, the entire piston sub-assembly (10, 20, 130, 160) can move in a distal longitudinal direction to compress the spring 50 inside the body tube 120 and this compression distance forms a space 134 (see FIG. 17) over which the force switch 1 functions as a switch.

The bias device (e.g., compression spring) 50 disposed between the puck 130 and the distal transverse surface of the widening 14 imparts a proximally directed force against the piston 10 when the puck 130 compresses the spring 50. This force, referred to herein as a pre-tension, keeps the contact screw 160 against the electrically conductive distal transverse surface of the contact pin 140. Without any external force imparted on the force switch 1, the pre-tension will always keep the contact pin 140 at this position and electrical contact between the first contact and the contact pin 140 will remain. A distally directed external force F imparted upon the tip 20 could alter this situation. See FIG. 17. If the force F is not as great as the pre-tension force imparted by the spring 50, then the spring 50 will not compress any further than it has already been compressed by the puck 130. However, if the force F is greater than the pre-tension force imparted to the piston 10 by the spring 50, then the spring 50 will compress further and the tip 20, along with the remainder of the piston sub-assembly (10, 130, 160) will move in a distal longitudinal direction. The distal longitudinal direction is limited by the greatest compression distance of the spring 50, which, in most applications of the force switch 1, will not occur. This configuration, therefore, provides an electrical switch that has an adjustable longitudinal pre-tension force that must be overcome before the switch 1 can actuate and complete the electrical circuit that is "closed" until the contact screw 160 no longer touches the contact pin 140. The switching distance of the force switch 1 of FIGS. 10 to 17 is defined by the longitudinal gap 112 existing between the proximal transverse surface of the stub 62 and the distal transverse surface of the widening 166. FIGS. 17 and 19 show the piston sub-assembly (10, 130, 160) in the actuated distal position and FIG. 16 shows the piston sub-assembly in the un-actuated proximal position.

One exemplary process for assembly of the force switch 1 of FIGS. 10 to 17, the distal end of the switch bushing 60 having the projecting stub 62 is fastened longitudinally to the proximal end of the body tube 120. The piston 10 inserted inside the body tube 120 and the spring 50 inserted over the central shaft 16 of the piston 10 inside the body tube 120. The puck 130 is placed over the distal end 12 of the piston 10 and the tip 20 is fully or partially screwed onto the exterior threads of the distal end 12 of the piston 10. At this point, if the tip is fully screwed onto the piston 10, the piston 10 will impart the pre-tension force onto the stub 62 of the switch bushing. To avoid this force, the tip 20 can be only partially screwed onto the distal end 12 of the piston 10. The contact screw 160 is, then, screwed into the internal bore 16 of the piston 10 at the proximal end thereof to capture the stub 62 between the widening 14 of the piston 10 and the widening 166 of the contact screw 160. This forms a piston-spring sub-assembly.

The mounting body 70 is longitudinally fixedly connected to the contact pin 140 with the insulating bushing 150 therebetween. Because of the nested shapes of these parts, the order of the connection is limited only by the costs and time for manufacturing the connections. Alternatively, the insulating bushing 150 and the contact pin 140 can be placed inside the distal end of the mounting body 70, but, in such a case, these two parts could move longitudinally if the distal end of the force switch 1 is tilted downward. This forms a contact pin sub-assembly.

The piston-spring and contact pin sub-assemblies are connected together by fastening, longitudinally, the mounting body 70 to the switch bushing 60. If the tip 20 is fully screwed onto the piston 10, then the fastening will have to overcome the pre-bias force of the spring 50. If, however, the tip 20 is minimally screwed onto the piston 10 such that no pre-bias exists in the spring 50, then, after all longitudinal fastening has occurred, the tip 20 can be fully screwed onto the distal end 12 of the piston 10 to place the spring 50 in the pre-tensioned state. The conductor of the insulated wire 206 is attached in the longitudinal bore 146 of the contact pin 140 to complete the circuit 300.

In each case of the normally open and normally closed configurations, the longitudinal gap 112 has a length of between approximately 25 μm (0.001") and approximately 750 μm (0.030"), or in a shorter range between approximately 75 μm (0.003") and approximately 200 μm (0.008").

The conductive parts of the force switch 1 can be of stainless steel, copper, nickel-plated copper, nickel-plated brass, for example. Where the conductor of the insulated wire 206 needs to be soldered, each of these materials will be sufficient.

The range of force that the force switch 1 applicable for switching between the two states can be between approximately 3 ounces to approximately 20 pounds, or a shorter range of approximately 5 pounds to approximately 8 pounds.

With regard to the mechanics of selecting the spring 50, the desired pre-tension force is selected to be within or at the mid-range of the range of a given spring 50. In other words, the change in state of the force switch will occur not close to a maximum of the spectrum of the spring 50 pre-tension but, instead, somewhere in the middle of the spectrum.

The circuitry described above only provides a binary output—whether or not the force on the external object that is transmitted through the force switch 1 is greater or less than the pre-tensioning. If the force switch is provided with a strain gauge, also referred to as a load cell, then a continuous force output can be displayed to the user in which, for example, a row of LEDs gradually light up dependent upon the amount of force or an LCD or LED numerical field increments numerical values corresponding to the amount of force imparted through the force switch 1.

The force switch 1 above will now be described with respect to use in an intraluminal anastomotic circular stapler as depicted, for example, in U.S. Pat. No. 5,104,025 to Main et al. ("Main"), and assigned to Ethicon Endo-Surgery, Inc. This reference is hereby incorporated herein in its entirety. As can be seen most clearly in the exploded view of FIG. 7 in Main, a trocar shaft 22 has a distal indentation 21, some recesses 28 for aligning the trocar shaft 22 to serrations 29 in the anvil and, thereby, align the staples with the anvils 34. A trocar tip 26 is capable of puncturing through tissue when pressure is applied thereto. FIGS. 3 to 6 in Main show how the circular stapler 10 functions to join two pieces of tissue together. As the anvil 30 is moved closer to the head 20, tissue is compressed therebetween, as particularly shown in FIGS. 5 and 6. If this tissue is overcompressed, this surgical stapling procedure might not succeed. The interposed tissue can be subject to a range of acceptable compressing force during surgery. This range is known and is dependent upon the tissue being stapled. The stapler shown in Main cannot indicate to the user any level of compressive force being imparted upon the tissue prior to stapling. However, if the force switch 1 described herein is substituted for the trocar shaft 22, then the stapler 10 will be capable of showing the user when the compressive force (acting along the longitudinal axis 2 of the force switch 1) has exceeded the pre-tension of the switch 1. This pre-tension can be selected by the user to have a value within the range of acceptable tissue compressive force.

Figure 10:
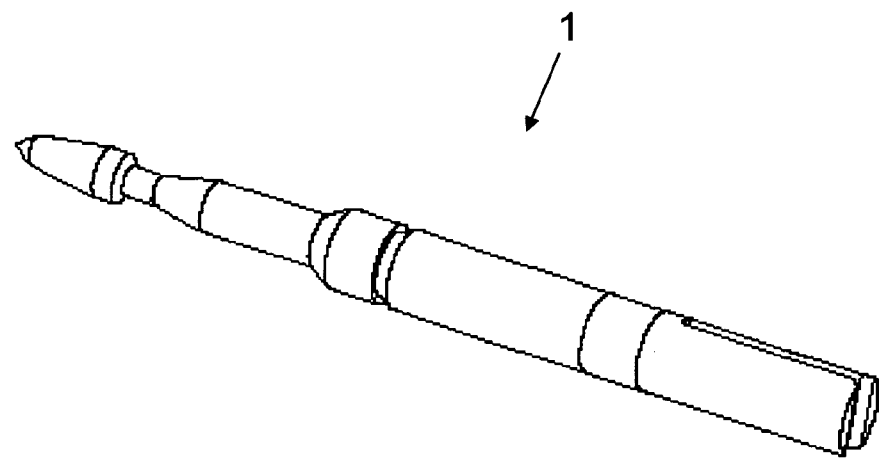
FIG. 10 is a perspective view from a side of another exemplary embodiment of a force switch according to the invention.
Figure 11:
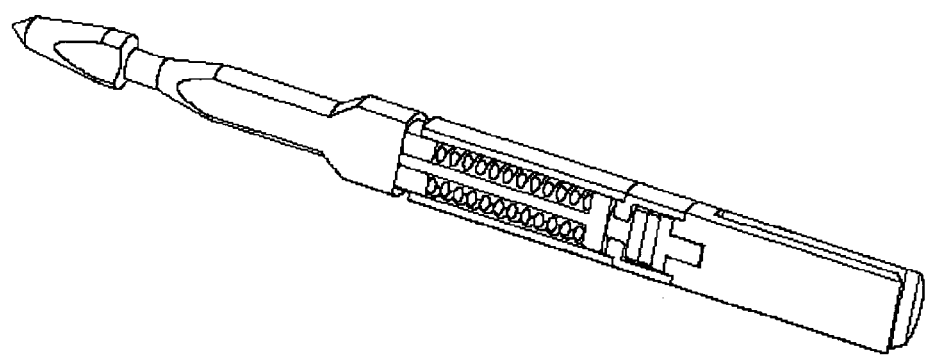
FIG. 11 is a longitudinally cross-sectional perspective view from a side of the force switch of FIG. 10 through a near half of the switch.
Figure 12:
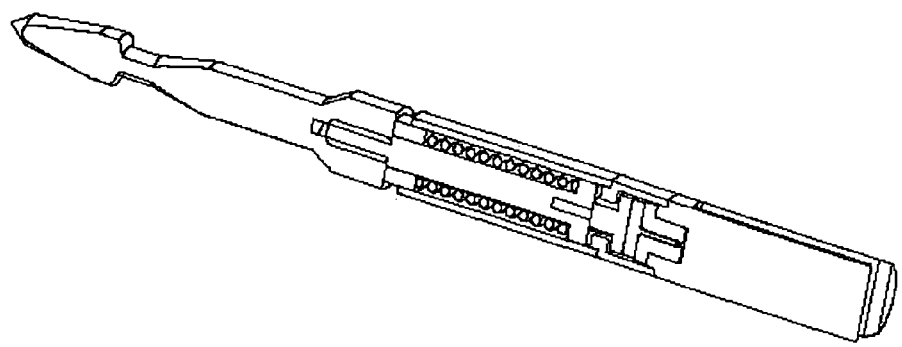
FIG. 12 is a longitudinally cross-sectional perspective view from a side of the force switch of FIG. 10 through a near half of the switch.

FIGS. 1 and 10 of the present application show a tip 20 having a pointed distal end that can function within at least the CDH surgical stapler manufactured and sold by Ethicon Endo-Surgery, Inc. The proximal end of the trocar shaft 22 in Main requires a male threaded screw for attachment to the head 20. Other circular staplers require an opposing tang embodiment that is shown in FIGS. 1 and 10 of the present application. Thus, the mounting body 70 can be in the form illustrated in FIGS. 1 to 17 or in the form shown in FIG. 7 in Main. The tip 20 and mounting body 70 can be customized to fit into any kind of similar surgical device.

The foregoing description and accompanying drawings illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

I claim:

1. A mechanical force switch to be disposed along a longitudinal device axis of a medical device, the switch comprising:
   an electrically conductive switching piston forming a first of two electrical contacts, said piston having:
      a longitudinal piston axis to be disposed parallel to the longitudinal device axis; and
      a bias-device contact;
   a hollow body defining a body interior cavity in which said piston is movably disposed along said piston axis to define:
      a switch-making piston position at a first longitudinal position with respect to said body; and
      a switch-breaking piston position at a second longitudinal position with respect to said body different from said first longitudinal position;
   an end stop defining a second interior cavity in which said piston is movably disposed, said end stop being at least partly disposed in said body interior cavity;
   a bias device being disposed about at least a portion of said piston between said end stop and said bias-device contact and imparting a variable longitudinal bias thereagainst to retain said piston in one of two positions selected from said switch-making position and said switch-breaking position until an external force imparted to said piston along said longitudinal piston axis exceeds said longitudinal bias and, when the external force exceeds said longitudinal bias, said piston moves to the other of said two positions, a magnitude of said longitudinal bias being dependent upon a longitudinal position of said end stop within said body interior cavity; and
   an electrically conductive second contact electrically insulated from said piston and forming a second of said two electrical contacts, said first and second electrical contacts being in said switch-making state when said piston is in said switch-making position and in said switch-breaking state when said piston is in said switch-breaking position.

2. The switch according to claim 1, wherein said longitudinal piston axis is to be disposed coincident with the longitudinal device axis.

3. The switch according to claim 1, wherein said bias device imparts said longitudinal bias to retain said piston in said switch-breaking position to create a normally open switch configuration.

4. The switch according to claim 1, wherein said bias device imparts said longitudinal bias to retain said piston in said switch-making position to create a normally closed switch configuration.

5. The switch according to claim 1, wherein a distance between said first longitudinal position and said switch-breaking position is between approximately 25 μm and approximately 750 μm.

6. The switch according to claim 1, wherein a distance between said first longitudinal position and said switch-breaking position is between approximately 75 μm and approximately 200 μm.

7. The switch according to claim 1, wherein a range of force to switch between said switch-making and switch-breaking states is between approximately 3 ounces and approximately 20 pounds.

8. The switch according to claim 1, wherein a range of force to switch between said switch-making and switch-breaking states is between approximately 5 pounds to approximately 8 pounds.

9. The switch according to claim 1, wherein said second contact is electrically insulated from said body and said piston.

10. The switch according to claim 1, further comprising a switch sub-assembly having:
  said electrically conductive second contact;
  a switch housing longitudinally fixedly and electrically conductively connected to said body and at least partially surrounding said second contact;
  a switch insulator electrically insulating said second contact from said switch housing; and
  a piston contact movably disposed in said housing and longitudinally fixedly and electrically conductively connected to said piston.

11. The switch according to claim 10, wherein:
  said switch insulator at least partially surrounds said piston contact;
  said electrically conductive second contact at least partially surrounds said switch insulator; and
  said switch housing at least partially surrounds said second contact, said switch insulator, and said piston contact.

12. The switch according to claim 10, wherein:
  said switch insulator at least partially surrounds said electrically conductive second contact; and
  said switch housing at least partially surrounds said second contact, said switch insulator, and said piston contact.

13. The switch according to claim 1, wherein:
  said piston has a first circular-shaped exterior;
  said bias-device contact has a second circular-shaped exterior having a larger diameter than said first circular-shaped exterior;
  said body interior cavity has a first circular-shaped interior substantially equal to said second circular-shaped exterior;
  said second interior cavity has a second circular-shaped interior substantially equal to said first circular-shaped exterior;
  said bias device has a third circular-shaped exterior substantially equal to said first circular-shaped interior; and
  said second contact has a fourth circular-shaped exterior smaller in diameter than said first circular-shaped interior.

14. The switch according to claim 1, wherein said piston, said end stop and said body form an assembly selected from the group consisting of:
  said end stop being threaded into said body interior cavity to longitudinally fix and rotationally adjust said end stop within body first interior cavity; and
  said end stop floating about said piston and within said body.

15. The switch according to claim 1, further comprising an electric indication circuit electrically connected to said first and second contacts and having an indicator transmitting state-change information to a user signaling that a state change of said piston has occurred.

16. The switch according to claim 1, wherein said bias device is a compression spring compressed between said bias-device contact and said end stop around said piston to bias said piston in a direction away from said end stop.

17. A mechanical force switch to be disposed along a longitudinal device axis of a medical device and electrically actuating a change of state when a predefined force along the longitudinal device axis is exceeded, the switch comprising:
  an electrically conductive switching piston forming a first of two electrical contacts of the switch, said piston having:
    a longitudinal piston axis to be disposed coincident with the longitudinal device axis;
    a piston portion having a first exterior; and
    a flange having a flange exterior; and
  a hollow body defining a first interior cavity having a first interior substantially equal to said flange exterior, said piston being movably disposed in said first interior cavity along said longitudinal piston axis to define:
    a switch-making piston position at a first longitudinal position with respect to said body; and
    a switch-breaking piston position at a second longitudinal position with respect to said body different from said first longitudinal position;
  an end stop defining a second interior cavity having a second interior substantially equal to said first exterior, said piston portion being movably disposed in said second interior cavity, said end stop being disposed in said first interior cavity and having:
    a bias-device contact surface; and
    a stop exterior substantially equal to said first interior;
  a bias device having a third exterior substantially equal to said first interior and being disposed about said piston portion between said bias-device contact surface and said flange, said bias device imparting a variable longitudinal bias against said flange to retain said piston in one of two positions selected from said switch-making position and said switch-breaking position until an external force imparted to said piston along said longitudinal piston axis exceeds said longitudinal bias and, when the external force exceeds said longitudinal bias, said piston moves to the other of said two positions, a magnitude of said longitudinal bias being dependent upon a longitudinal position of said end stop within said first interior cavity; and
  a switch assembly having:
    a housing longitudinally connected to said hollow body;
    a switch sub-assembly longitudinally connected to said piston and movably disposed in said housing, said sub-assembly having:
      a switch insulator; and
      an electrically conductive second contact electrically insulated from said piston, said first and second contacts being in said switch-making state when said piston is in said first longitudinal position and in said switch-breaking state when said piston is in said second longitudinal position.

18. The switch according to claim 17, wherein:
  said piston has a proximal end and said flange is at said proximal end;
  said end stop is threaded into said first interior cavity to longitudinally fix and rotationally adjust said end stop within said first interior cavity; and
  said piston portion is slidably disposed in said second interior cavity.

19. A mechanical force switch to be disposed along a longitudinal device axis of a medical device and electrically actuating a change of state when a predefined force along a longitudinal axis of a device is exceeded, the switch comprising:
  a switching piston defining an internal cavity and having:

a first portion having a first exterior;
a second portion having:
    a second exterior; and
    an outer flange with a flange exterior;
at least one electroconductive portion forming a first of two contacts of an electrical switch for signaling a switching state of said piston; and
a longitudinal piston axis to be disposed coincident with the longitudinal device axis;
a hollow body defining:
    a first interior cavity having a first interior; and
    a second interior cavity having a second interior substantially equal to said flange exterior, said piston being movably disposed in said first and second interior cavities along said longitudinal piston axis to define:
        a switch-making piston position at a first longitudinal position with respect to said body; and
        a switch-breaking piston position at a second longitudinal position with respect to said body different from said first longitudinal position;
at least one adjustable end stop:
    having a stop exterior substantially equal to said first interior; and
    defining a stop interior cavity having a stop interior substantially equal to said first exterior;
a bias device having a bias exterior substantially equal to said second interior and disposed about said first portion between said end stop and said outer flange, said bias device imparting a variable longitudinal bias against said outer flange to retain said piston in one of two positions selected from said switch-making position and said switch-breaking position until an external force imparted to said piston along said longitudinal piston axis exceeds said longitudinal bias and, when the external force exceeds said longitudinal bias, said piston moves to the other of said two positions, a magnitude of said longitudinal bias being dependent upon a longitudinal position of said end stop within said first interior cavity; and
a switch assembly longitudinally connected to said body and having:
    a switch insulator; and
    an electrically conductive second contact electrically insulated from said piston, said first and second contacts being in said switch-making state when said piston is in said first longitudinal position and in said switch-breaking state when said piston is in said second longitudinal position.

20. The switch according to claim 19, wherein:
said second interior permits longitudinal sliding translation of said outer flange within said second interior cavity; and
said stop interior slidably receives said first portion of said piston therein.

21. The switch according to claim 19, wherein:
said piston has a proximal end and said outer flange is at said proximal end;
said end stop is threaded into said first interior cavity to longitudinally fix and rotationally adjust said end stop within said first interior cavity; and
said piston portion is slidably disposed in said stop interior cavity.

22. The switch according to claim 19, wherein:
said first portion is a distal portion;
said second portion is a proximal portion;
said first interior cavity is a distal cavity having interior threads;
said second interior cavity is a proximal cavity;
said first interior of said distal cavity is larger than said second interior of said proximal cavity; and
said end stop has exterior threads mating with said interior threads.

* * * * *